United States Patent
Devos et al.

(10) Patent No.: US 10,247,659 B2
(45) Date of Patent: Apr. 2, 2019

(54) DEVICE FOR CHARACTERIZING AN INTERFACE OF A STRUCTURE AND CORRESPONDING DEVICE

(71) Applicants: MENAPIC, Lille (FR); CENTRE NATIONAL DE LA RECHERCHE SCIENTIFIQUE (C.N.R.S.), Paris (FR)

(72) Inventors: Arnaud Devos, Ennetieres en Weppes (FR); Patrick Emery, Lille (FR); Arnaud Le Louarn, Lys lez Lannoy (FR)

(73) Assignee: MENAPIC, Lille (FR)

( * ) Notice: Subject to any disclaimer, the term of this patent is extended or adjusted under 35 U.S.C. 154(b) by 142 days.

(21) Appl. No.: 15/305,773

(22) PCT Filed: Apr. 24, 2015

(86) PCT No.: PCT/FR2015/000084
§ 371 (c)(1),
(2) Date: Oct. 21, 2016

(87) PCT Pub. No.: WO2015/166146
PCT Pub. Date: Nov. 5, 2015

(65) Prior Publication Data
US 2017/0045440 A1     Feb. 16, 2017

(30) Foreign Application Priority Data
Apr. 30, 2014   (FR) ...................................... 14 53969

(51) Int. Cl.
*H01S 1/00*       (2006.01)
*H04B 10/2537*    (2013.01)
(Continued)

(52) U.S. Cl.
CPC ....... *G01N 21/1702* (2013.01); *G01N 21/636* (2013.01); *G01N 2021/1706* (2013.01); *G01N 2021/638* (2013.01)

(58) Field of Classification Search
CPC ........... G01N 21/1702; G01N 21/1704; G01N 21/1706; G01N 21/636; G01N 2021/638;
(Continued)

(56) References Cited

U.S. PATENT DOCUMENTS 4,710,030 A   12/1987   Tauc
5,633,711 A    5/1997   Nelson
(Continued)

OTHER PUBLICATIONS

Devos et Al Giant oscillations in the picosecond ultrasonics response of crystalline silicon: Connection with the electronic structure World Congress on Ultrasonics Sep. 7, 2003, pp. 1197-1200 XP002385317.
(Continued)

*Primary Examiner* — Lisa M Caputo
*Assistant Examiner* — Suman K Nath (57) ABSTRACT

The present invention relates to a device (1) for characterizing an interface of a structure (6), said structure (6) comprising a solid first material and a second material, the materials being separated by said interface. The device (1) comprises:
   means (2) for generating a first mechanical wave;
   means (2) for forming Brillouin oscillations;
   means (10) for detecting time variation of the Brillouin oscillations;
   means (12) for responding to the time variation of the Brillouin oscillations to identify reflection of said first mechanical wave by said interface or transmission through said interface of a second mechanical wave interfering with the first mechanical wave; and
(Continued)

means (13) for determining the variation in amplitude of the Brillouin oscillations before and after reflection or transmission by said interface.

The invention also relates to a corresponding method of characterization.

14 Claims, 4 Drawing Sheets

(51) Int. Cl.
  *G01N 21/17* (2006.01)
  *G01N 21/63* (2006.01)

(58) Field of Classification Search
  CPC ........... G01N 2291/04; G01N 29/4436; G01N 29/4454; H01S 1/00; H04B 10/2537; G01D 5/35364
  USPC .................. 73/655, 620, 627, 615, 649, 643
  See application file for complete search history.

(56) References Cited

U.S. PATENT DOCUMENTS

| | | | |
|---|---|---|---|
| 5,748,318 A | 5/1998 | Maris | |
| 6,069,703 A | 5/2000 | Banet | |
| 6,087,242 A | 7/2000 | Maris | |
| 7,181,137 B1 * | 2/2007 | Tamburello | H04B 10/032 398/10 |
| 7,852,488 B2 | 12/2010 | Devos | |
| 2001/0028460 A1 | 10/2001 | Maris et al. | |
| 2010/0332203 A1 | 12/2010 | Maris | |
| 2016/0172254 A1 | 6/2016 | Wimplinger | |

OTHER PUBLICATIONS

Sadtler Sabrina et Al Hypersound damping in vitreous silica measured by ultrafast acoustics International Journal of Thermophysics Springer New York USA vol. 34, No. 8 Sep. 15, 2013, pp. 1785-1794.

Devos et Al A different way of performing picosecond ultrasonic measurements in thin transparent films based on laser-wavelength effects Applied Physics Letters 86, 211903 (2005) 0003-6951/2005/86(21)/211903/3.

Thomsen et Al Picosecond interferometric technique for study of phonons in the brillouin frequency range Optics Communications, Oct. 15, 19986 vol. 60, No. 1, 2 0 030-4018/86 Elsevier Science Publishers B.V.

Picosecond Ultrasonics: possible connections with interband transition Physics Review Letters Mar. 12, 2001, vol. 86, No. 12.

Devos et al A novel approach to picosecond ultrasonics at variable laser-wavelength for the characterization of the aluminium nitride films used for microsystem applications. World Congress on ultrasonics (Paris, Sep. 7-10, 2003), pp. 793-796 ISBN 2-9521105-0-6.

* cited by examiner

FIG.7

DEVICE FOR CHARACTERIZING AN INTERFACE OF A STRUCTURE AND CORRESPONDING DEVICE

BACKGROUND OF THE INVENTION

The present invention relates to the field of measuring structural properties. More precisely, the present invention relates to characterizing a structure by means of a soundwave that is generated and detected by a light pulse.

U.S. Pat. No. 5,748,318 discloses a system for characterizing thin films and interfaces between such films by measuring their mechanical and thermal properties. In the system described, light is absorbed in the thin layer or in a structure made up of a plurality of thin layers, and the modifications to light reflection and transmission are analyzed. The change in reflection or transmission is used to provide information about ultrasound waves produced in the structure. As a result, it is possible to determine the thicknesses of layers and also several optical properties of the structure.

U.S. Pat. No. 5,748,318 is thus an example implementation of a pump-probe system known to the person skilled in the art. In such a system, the light source is a laser emitting short pulses (e.g. femtosecond pulses) at a fixed wavelength so as to produce a first beam that is split in a splitter into a "pump" beam and into a "probe" beam. Thereafter, the light path of the probe beam or the light path of the pump beam is varied by a mirror that is servo-controlled in position. It is then known that the properties of the structure under the effect of the emitted beams give rise to modification in the reflection (or transmission) properties of the probe wave. In particular, and in known manner, by observing the modification in reflection as a function of time, it is possible to determine echoes that are characteristic of interfaces of a structure. Analyzing the echo signal then makes it possible, by way of example, to deduce the thickness of the material, if the speed of propagation of the soundwave in the medium is known.

In order to increase the number of characteristics that are extracted, and in particular both speed and thickness, the publication *Evidence of laser-wavelength effect in picosecond ultrasonics: possible connections with interband transition* (Physics Review Letters, Mar. 12, 2001, Volume 86, Number 12) describes the use of a pump-probe device as described above, but associated with a wavelength-tunable laser, thus enabling the wavelength of the emitted signals to be varied.

As a result of these wavelength effects, it is possible to access both thickness characteristics and speed characteristics in certain types of structure. Specifically, as described in the publication *A novel approach using picosecond ultrasonics at variable laser-wavelength for the characterization of aluminum nitride films used for microsystem applications* (A. Devos, G. Caruyer, C. Zinck, and P. Ancey, World Congress on Ultrasonics (Paris Sep. 7-10, 2003), pp. 793-796 ISBN 2-9521105-0-6), for a structure that is transparent to the probe beam, an acousto-optical interaction appears within the material giving rise to the appearance of oscillations instead of simple pulses observed by echo. Those oscillations are known as "Brillouin" oscillations and they have a period that depends on the wavelength of the probe and on the speed of sound in the material.

Another example of a device making use of Brillouin oscillations is also described in patent application FR 2 887 334.

Nevertheless, the number of characteristics that are measurable using those methods remains limited, and it is not possible in particular to characterize accurately a surface or an interface.

OBJECT AND SUMMARY OF THE INVENTION

The present invention seeks to solve the various technical problems set out above. In particular, the present invention seeks to propose a device enabling an interface of a structure to be characterized in reliable manner. More particularly, the present invention seeks to propose a device making it possible in reliable manner to characterize a surface of the structure, e.g. its roughness, or an interface between two layers of the structure, e.g. its acoustic transmission coefficient.

Thus, in one aspect, there is provided a device for characterizing an interface of a structure, said structure comprising a solid first material and a second material, which materials are separated by said interface. The device comprises:
  means for generating a first mechanical wave in the first material, e.g. means for generating pump radiation;
  means for forming Brillouin oscillations, comprising means for generating probe radiation configured to propagate at least in part in the first material;
  means for detecting the variation in time of the Brillouin oscillations in particular in the first material;
  identification means configured to use the time variation of the Brillouin oscillations in particular in the first material to identify reflection of said first mechanical wave by said interface or transmission through said interface of a second mechanical wave interfering with the first mechanical wave; and
  determination means configured to determine the variation in amplitude of the Brillouin oscillations in particular in the first material before and after reflection or transmission by said interface.

By monitoring the variations in the amplitude of the Brillouin oscillations, it is possible to evaluate certain physical parameters of the structure. More precisely, since the Brillouin oscillations are formed by a soundwave propagating over a certain distance in the structure, it is possible to observe and make use of wave phenomena suitable for characterizing the structure, e.g. interference phenomena between a plurality of waves or indeed the effects of diffraction by surface irregularities, in particular.

Preferably, the determination means are configured to determine the variation in amplitude of the Brillouin oscillations as a function of the wavelength of the probe radiation. Analyzing the Brillouin oscillations at different wavelengths makes it possible to refine the characterization of the structure, or indeed to determine additional characteristics.

In an embodiment, the second material presents an acoustic impedance that is very different from the acoustic impedance of the first material, for example it is a gas, and: the identification means are configured to identify a reflection of said first mechanical wave by said interface, and the determination means are configured to determine the variation in amplitude of the Brillouin oscillations before and after reflection by said interface, in order to characterize the roughness of said interface.

In this embodiment, transmission of the soundwave by said interface in the second material may be made to be negligible, in particular when the impedance of the second material is much greater than that of the first material (the soundwave is reflected with a change of sign at the interface)

or indeed when the impedance of the first material is much greater than that of the second material (the soundwave is reflected at the interface without change of sign). Thus, the second material may be a gas, e.g. air, i.e. said interface may be a free surface of the first material.

In this embodiment, the device makes it possible to characterize the surface properties of the structure, e.g. roughness, by comparing the amplitude of the Brillouin oscillations before and after reflection by said surface. The surface irregularities then give rise to a phenomenon of the soundwave being diffracted, which causes the reflected soundwave to disperse, and thus leads to variation in the amplitude of the measured Brillouin oscillations.

Preferably, the means for generating probe radiation are configured to change the wavelength of the probe radiation as a function of the size of the roughness to be measured. Characterization of an article by monochromatic radiation is limited by the wavelength of said radiation. In the present circumstances, by varying the wavelength of the probe radiation, characterization makes use of soundwaves that have different frequencies due to repetitive patterns in the surface of the structure. Thus, varying the wavelength makes it possible to characterize different repetitive patterns in the surface of the structure, i.e. its roughness.

In another embodiment, the second material is a solid thin layer, and: the identification means are configured to identify transmission by said interface of a second mechanical wave interfering with the first mechanical wave, and the determination means are configured to determine the variation in amplitude of the Brillouin oscillations before and after transmission by said interface of the second mechanical wave, in order to characterize the acoustic transmission coefficient of said interface.

In this embodiment, interference takes place between two waves, one of which has been transmitted through an interface. Depending on the amplitude of the interference, as determined by the Brillouin oscillations, it becomes possible to evaluate the amplitude of the waves transmitted by the interface, and thus the transmission coefficient of the interface.

Preferably, the means for generating a first mechanical wave in the first material are configured to form the first and second mechanical waves simultaneously respectively in the first material and in the second material. More precisely, the two mechanical waves are formed at the interface between the first and second materials, the first wave propagating in the first material and the second wave propagating in the second material. Since the second material is a layer that is thin, the second wave is quickly reflected by the second surface of the second layer and returns towards the interface between the first and second materials, with a fraction thereof passing through the interface, depending on the transmission coefficient of said interface, so as to form the second mechanical wave in the first material. Since the second mechanical wave was formed at the same time as the first mechanical wave, the two waves are mutually coherent and they can therefore interfere, thereby leading to variation in the amplitude of the measured Brillouin oscillations.

Preferably, the device further comprises adjustment means for adjusting parameters of a theoretical model giving the values for variation in amplitude of the Brillouin oscillations for different probe radiation wavelengths, in order to obtain the amplitude variation of the Brillouin oscillations as determined by the determination means, with the parameters as adjusted in this way serving to characterize the interface, and in particular the acoustic transmission coefficient of the interface.

Using a theoretical model, it is possible to predict the form of the Brillouin oscillations that can be obtained from a structure having characteristics (dimensions, quality, materials, . . . ) that constitute the parameters of the theoretical model. Thus, by adjusting the parameters of the theoretical model in order to obtain the Brillouin oscillations as observed, it becomes possible to discover the characteristics of the structure under study, e.g. the thickness of a layer, the transmission coefficient of an interface, or indeed the speed of sound in the layer. Furthermore, since such adjustment is performed over a greater or lesser number of values, it is possible to select the accuracy desired for the results that are obtained.

Preferably, the means for generating pump radiation and the means for generating probe radiation are identical or they are different.

The means for generating pump radiation and the means for generating probe radiation may comprise one or two tunable laser sources.

Alternatively, they may comprise two means for emitting a continuum of light.

Alternatively, the means for generating pump radiation may comprise a fixed laser source, and the means for generating probe radiation may comprise a tunable laser source.

In another aspect, the invention also provides a method of characterizing an interface of a structure, said structure comprising a solid first material and a second material, which materials are separated by said interface. The method comprises the following steps:
  forming a first mechanical wave in the first material, e.g. with pump radiation;
  forming Brillouin oscillations with probe radiation propagating at least in part in the first material;
  detecting the time variation of the Brillouin oscillations in particular in the first material;
  identifying reflection of said first mechanical wave by said interface or transmission through said interface of a second mechanical wave interfering with the first mechanical wave on the basis of the time variation of the Brillouin oscillations, in particular in the first material; and
  determining the variation in amplitude of the Brillouin oscillations, in particular in the first material before and after reflection or transmission by said interface.

Preferably, the variation in amplitude of the Brillouin oscillations as a function of the wavelength of the probe radiation is determined.

In an implementation, the second material presents acoustic impedance that is very different from the acoustic impedance of the first material, for example it is a gas, and: a reflection of said first mechanical wave by said interface is identified, and the variation in amplitude of the Brillouin oscillations before and after reflection by said interface is determined in order to characterize the roughness of said interface.

Preferably, the wavelength of the probe radiation is selected as a function of the size of the roughness to be measured.

In another implementation, the second material is a solid thin layer, and: transmission through said interface of a second mechanical wave interfering with the first mechanical wave is identified, and the variation in amplitude of the Brillouin oscillations before and after transmission by said interface of the second mechanical wave is determined in order to characterize the acoustic transmission coefficient of said interface.

Preferably, the first and second mechanical waves are formed simultaneously respectively in the first material and in the second material.

Preferably, the parameters of a theoretical model giving the values for variation in amplitude of the Brillouin oscillations for different wavelengths of the probe radiation are adjusted in order to obtain the variations in amplitude of the Brillouin oscillations as determined, with the parameters as adjusted in this way serving to characterize the interface and in particular the acoustic transmission coefficient of the interface.

BRIEF DESCRIPTION OF THE DRAWINGS

The invention and its advantages can be better understood on reading the following detailed description of a particular embodiment given by way of non-limiting example and illustrated in the accompanying drawings, in which.

DETAILED DESCRIPTION OF THE INVENTION

Figure 1:
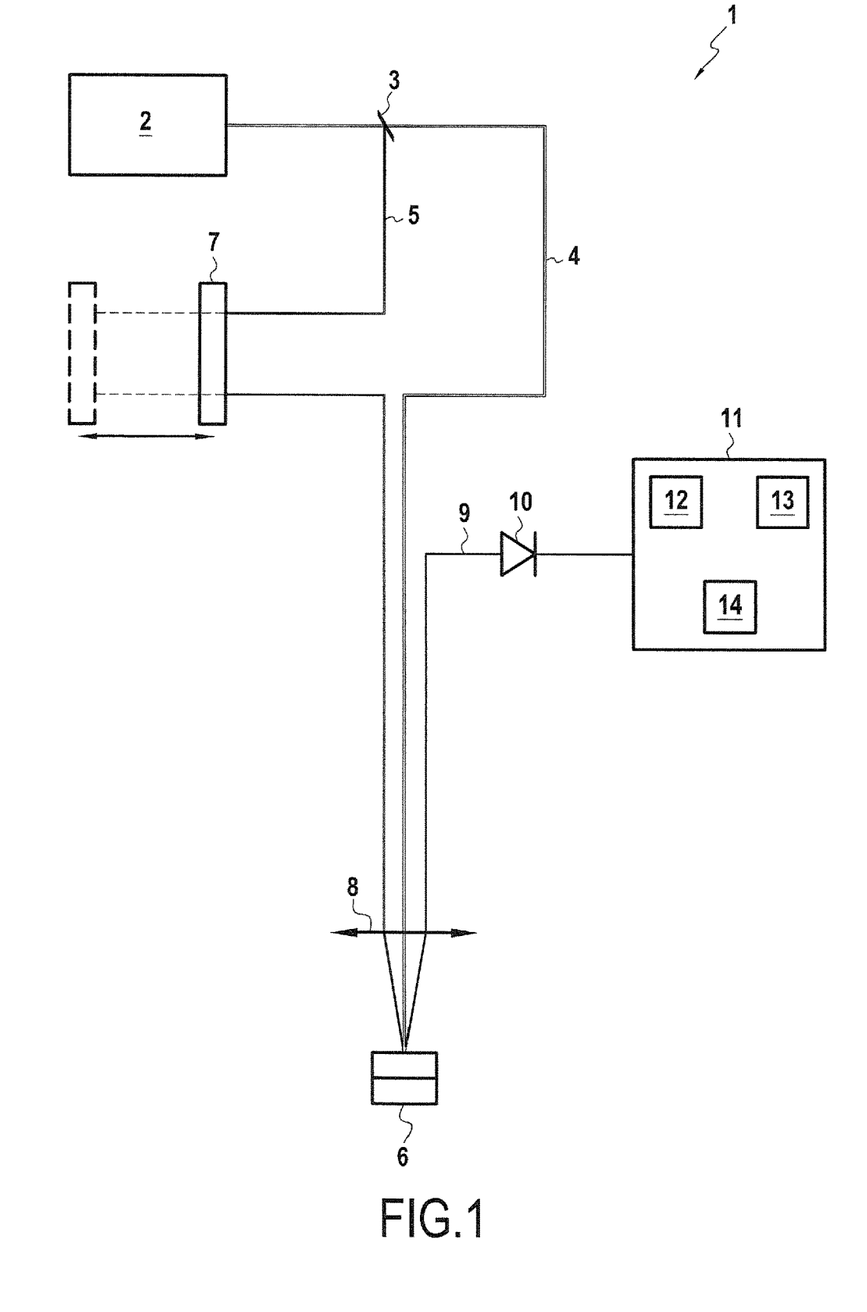
FIG. 1 is a diagrammatic view of a characterization device of the invention.

FIG. 1 is a diagram showing an embodiment of a characterization device 1 of the invention.

The device 1 thus comprises a short-pulse laser source 2. The short pulses from the laser need to be matched to the desired time resolution. It is possible to envisage using pulses of the order of 1 picosecond (ps) or 0.1 ps.

In a first embodiment, this source is wavelength tunable by means of a suitable oscillator, e.g. of the titanium:sapphire type, capable of producing 120 femtosecond (fs) pulses at a repetition rate of 76 megahertz (MHz) or indeed 80 MHz, centered on a wavelength that is suitable over the range 700 nanometers (nm) to 990 nm, or indeed over the range 680 nm to 1070 nm.

The source produces radiation that is split by a splitter 3 into pump radiation 4 and probe radiation 5, both of which are to interact with the structure 6 for analysis.

The probe radiation 5 is subjected to path length variation compared with the pump radiation 4, e.g. by means of a movable mirror 7 that is servo-controlled in position, so as to reach the structure 6 with a time offset relative to the pump radiation.

It is then focused on the structure 6 by an optical system 8, and it is reflected in the form of a signal 9 to detector means 10, e.g. of the photodetector type, in order to generate a signal that can be analyzed by processor means 11, e.g. a conventional type of computer suitable for performing the processing of the invention.

Alternatively, the probe signal may also be detected after transmission through the structure 6.

In order to ensure that the signals pass properly from the source to the structure, the optical system is adapted to accommodate the variation in wavelength from the source. The person skilled in the art knows how to adapt such an optical system depending on the selected sources and wavelength ranges, and only a few examples of suitable optical systems are described herein.

The optical systems should preferably be broadband systems, both concerning the mirrors and the treated lenses. In order to achieve a sufficient signal-to-noise ratio, pump-probe devices make use of modulation of the pump radiation and demodulation of the probe radiation. The modulation must be performed outside the noise range of the laser, typically at several 100 kilohertz (kHz). It is performed by an acousto-optical modulator that acts like an electrically controlled grating, or indeed by an electro-optical modulator, or indeed by an optical chopper. The way the grating diffracts the pump radiation varies with wavelength. Thus, by changing the wavelength, the pump radiation is caused to vary in direction, which means that the device can lose its adjustment. It is therefore possible to use an acousto-optical modulator that can be controlled using an electrical signal of variable frequency. Varying deflection of the pump radiation is thus compensated by changing the pitch of the electrically generated grating.

When using a half-wavelength that is obtained by optical doubling in a non-linear crystal, e.g. of the beta barium borate (BBO) type, doubling relies on a phase tuning condition in the crystal, which is associated with its orientation relative to the radiation. The change in wavelength needs to be taken up over this angle. This step is performed manually or automatically.

The person skilled in the art readily understands that the pump and probe beams may also be generated by two distinct sources. Under such circumstances, the sources may themselves be movable in order to generate the variation in the optical path length of the probe radiation relative to the pump radiation. It is also possible to use a laser source of fixed wavelength and a source that is tunable.

In a second embodiment, the source 2 serves to generate a light continuum extending over a broad range of wavelengths. Under such circumstances, the detector means 10 may comprise a spectrometer (not shown) for analyzing the intensity of the received light prior to transmitting the signal for analysis to the processor means 11. It is also possible to use any system of filters in front of an ordinary photodetector.

The plurality of wavelengths is then generated continuously, e.g. by a fixed wavelength femtosecond laser associated with an optical fiber.

In general manner, any type of source suitable for generating short laser pulses corresponding to a discrete or continuous set of wavelengths may be used.

Likewise, it is possible to use any means suitable for producing a time offset between the pump radiation and the probe radiation. This offset can thus be produced by varying the optical path length as described above, or by means enabling the arrival time of one pulse to be adjusted relative to another.

The processor means 11 comprise identification means 12 and determination means 13.

The identification means 12 receive the variation over time in the signals detected by the detector means 10, and in particular the Brillouin oscillations. The identification means 12 are configured to identify, from the received signal, a reflection of a mechanical wave on the interface of the structure, or indeed a transmission of a mechanical wave through the interface of the structure.

An identification of Brillouin oscillations before and after reflection or transmission is then transmitted to the determination means 13, which are configured to determine the variation in amplitude of said Brillouin oscillations before and after reflection or transmission. Thus, the determination means 13 can calculate the ratio of the maximum amplitude of the Brillouin oscillations before reflection or transmission to the maximum amplitude of the Brillouin oscillations after reflection or transmission. The determination means 13 may also take account of a phase shift before and after reflection or transmission.

Preferably, when the means for generating the probe radiation can emit probe radiation at different wavelengths, the determination means are configured to determine the variation in amplitude, before and after reflection or transmission of the Brillouin oscillations as a function of the wavelength of the probe radiation.

Finally, the characterization device 1 may comprise adjustment means 14 for adjusting parameters of a theoretical model. The adjustment means 14 include a theoretical model predicting the variation in amplitude of the Brillouin oscillations as a function of certain structural characteristics (thicknesses, materials, etc.) of the structure being analyzed, and by modifying these parameters it can cause the results that are obtained experimentally to coincide with the results from the theoretical model. Under such circumstances, when the structure of the theoretical model corresponds to the structure being analyzed, it becomes possible to know the structural characteristics of the structure being analyzed by using the parameters obtained by the adjustment means 14.

There follows a description of two embodiments and uses of the FIG. 1 characterization device 1.

In one embodiment, the device 1 is used to characterize an interface I between a substrate and a thin layer. Thus (see FIG. 2), the structure 100 being analyzed comprises a substrate 101 that is preferably transparent and of determined thickness, having a thin layer 102 arranged thereon, which layer is preferably absorbent. The structure 100 is arranged in the device 1 so that the probe radiation S passes initially through the substrate 101 and subsequently the thin layer 102. The structure 100 may thus be a sample of a solar panel comprising a glass substrate with an electrode arranged thereon.

Figure 2:
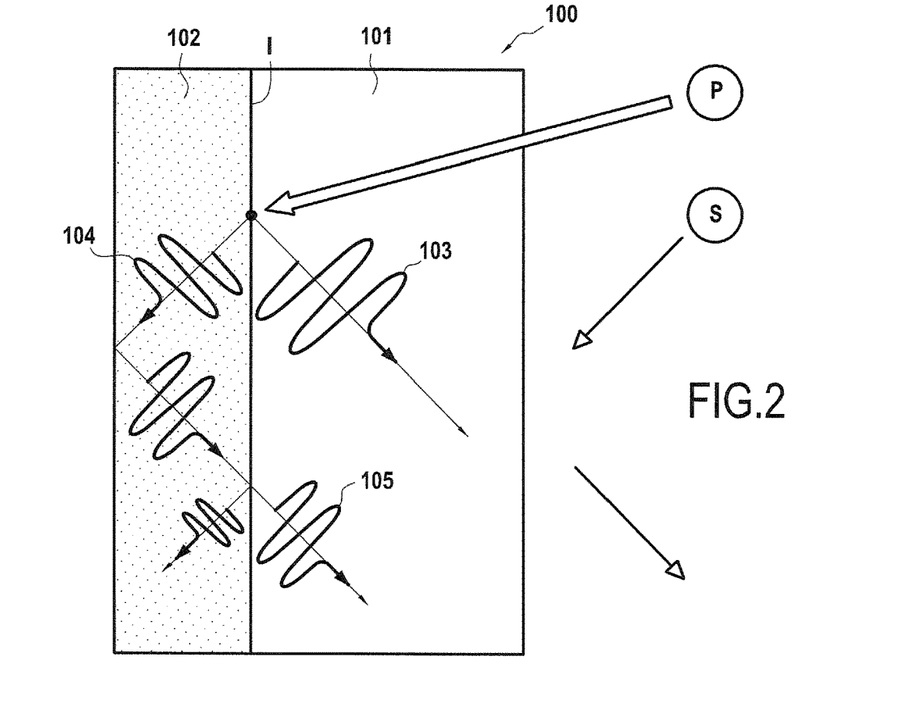
FIG. 2 shows a first implementation of the invention.

The thin layer 102 is selected so as to absorb the pump radiation P. Thus, the soundwave produced by the pump radiation is formed at the interface I between the substrate 101 and the thin layer 102.

Two soundwaves are then observed: a first soundwave 103 that propagates in the substrate 101 towards the free surface (that receives the probe radiation S), and a second soundwave 104 that propagates in the thin layer 102. Since the thin layer 102 presents thickness that is very small, the soundwave 104 propagating therein is reflected by the opposite surface of the thin layer 102 and returns towards the interface I through which it passes to a greater or lesser extent depending on the transmission coefficient of said interface I.

The fraction of the second soundwave 105 passing through the interface I is coherent with the first soundwave 103, and can thus interfere therewith. Depending on the phase difference between the two soundwaves 103 and 105, and depending on their respective amplitudes, the interference is pronounced to a greater or lesser extent. The characterization device 1 makes it possible to observe the Brillouin oscillations due to the first soundwave 103 and then due to the interference between the first and second soundwaves 103 and 105. It is thus possible to determine the amplitude of the fraction of the second soundwave 105 that has interfered with the first soundwave 103, and to deduce therefrom the transmission coefficient of the interface I.

In particular, the processor means 11 serve firstly to identify (using the means 12) the moment in the observation of the Brillouin oscillations at which the fraction of the second soundwave 105 interferes with the first soundwave 103, and then secondly to measure the variation in the amplitude of the Brillouin oscillations due to the interference (by using the means 13).

Preferably, the processor means 11 can perform this analysis for different wavelengths, and then use the means 14 to compare the results obtained with a theoretical model in order to refine the structural parameters of the sample.

Figure 3:
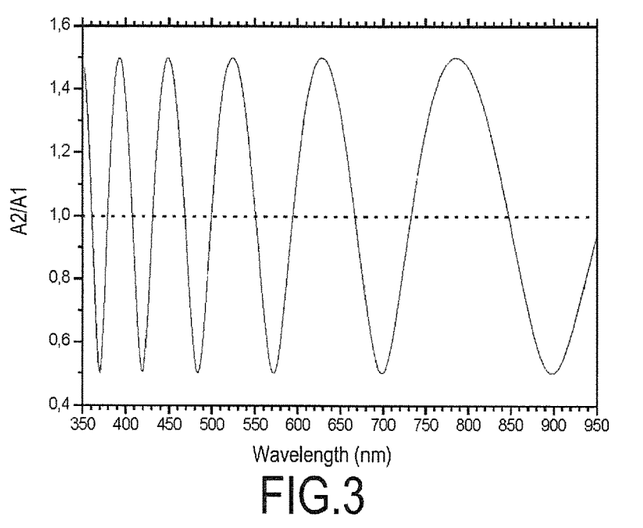
FIG. 3 shows an example of a result that can be obtained in the first implementation of the invention.

FIG. 3 shows an example of a result obtained by a theoretical model: the figure shows how the ratio A2/A1 (where A1 is the amplitude of the Brillouin oscillations corresponding to the first soundwave 103 and A2 is the amplitude of the Brillouin oscillations corresponding to interference between the first soundwave 103 and the fraction of the second soundwave 105) varies as a function of the wavelength of the probe radiation. In particular, the amplitude of the curve that is obtained (difference between the smallest ratio A2/A1 and the largest ratio A2/A1) enables the interface I between the two materials to be characterized, and the wavelength differences between two successive extremums enables the thickness of the thin layer to be characterized.

Alternatively, the structure being analyzed may be a multilayer structure having a plurality of thin layers on the transparent substrate. Under such circumstances, the successive interferences with the waves transmitted by the various thin layers can also be used as interpreted in order to characterize the interfaces between the various thin layers.

In another embodiment, the device 1 is used for characterizing the roughness of a surface of a given layer. Thus (see FIG. 4), the structure 200 being analyzed mainly comprises a preferably transparent given layer 201 that presents a free surface 202 of roughness that is to be determined, and an absorbent layer (not shown) arranged on the surface opposite from the free surface 202. The structure 200 is arranged in the device 1 in such a manner that the probe radiation S passes firstly through the free surface 202 for analysis, then through the given layer 201, and then through the absorbent layer.

Figure 4:
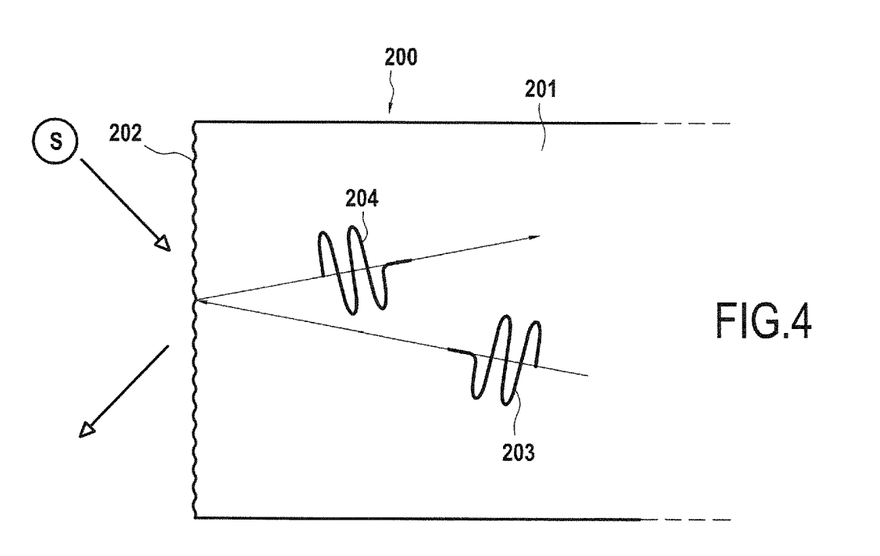
FIG. 4 shows a second implementation of the invention.

Alternatively, instead of a free surface 202, it would be possible to provide a layer of a second material presenting acoustic impedance that is very different from the acoustic impedance of the given layer 201 (i.e. much greater than or much less than said impedance), in order to obtain almost complete reflection of the soundwave at the interface.

The absorbent layer is selected so as to absorb the pump radiation. Thus, the soundwave produced by the pump radiation is formed at the interface between the given layer 201 and the absorbent layer.

A first soundwave 203 is then observed that propagates from the absorbent layer towards the free surface 202 of the given layer 201, followed by a second soundwave 204 that is due to the first soundwave 203 being reflected on the free surface 202 and propagating towards the absorbent layer.

The waveform of the second soundwave 204 then depends on the quality of the free surface 202 of the given layer, and in particular on its roughness, that enables reflection to take place more or less correctly. Thus, depending on the roughness of the free surface 202, the second soundwave 204 becomes spatially dispersed to a greater or lesser extent.

The characterization device 1 enables the Brillouin oscillations due to the first soundwave 203 and then to the second soundwave 204 to be observed. It is thus possible to estimate the roughness of the free surface 202 that reflected the soundwave.

In particular, the processor means 11 make it possible firstly to use the means 12 to identify the moment in the observation of the Brillouin oscillations at which the first soundwave reflects on the free surface 202 of the given layer in order to form the second soundwave, and then secondly to measure the variation in the amplitude of the Brillouin oscillations due to the reflection (by using the means 13).

The processor means can preferably perform this analysis at different wavelengths.

Figure 5:
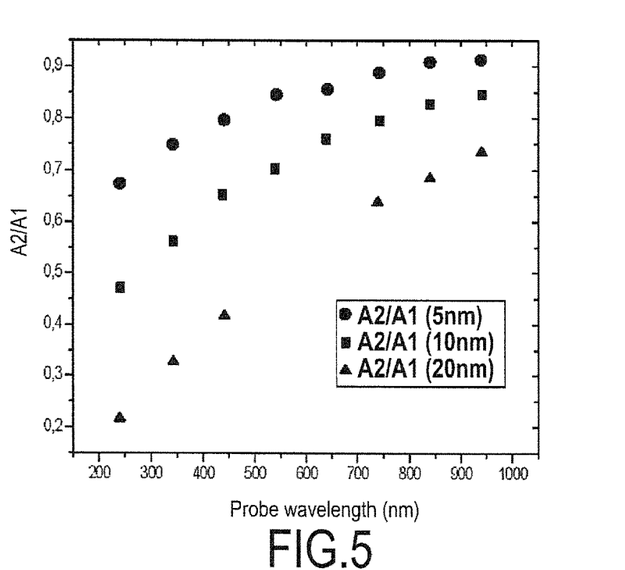
FIG. 5 shows an example of a result that can be obtained in the second implementation of the invention.

FIG. 5 gives an example of the results obtained for different roughnesses of the free surface (5 nm, 10 nm, and 20 nm) and for different wavelengths of the probe radiation. It can be seen in particular that by shortening the wavelength of the probe radiation S, it is possible to analyze higher frequency soundwaves that are more sensitive to the same irregularities of the free surface.

Figure 6:
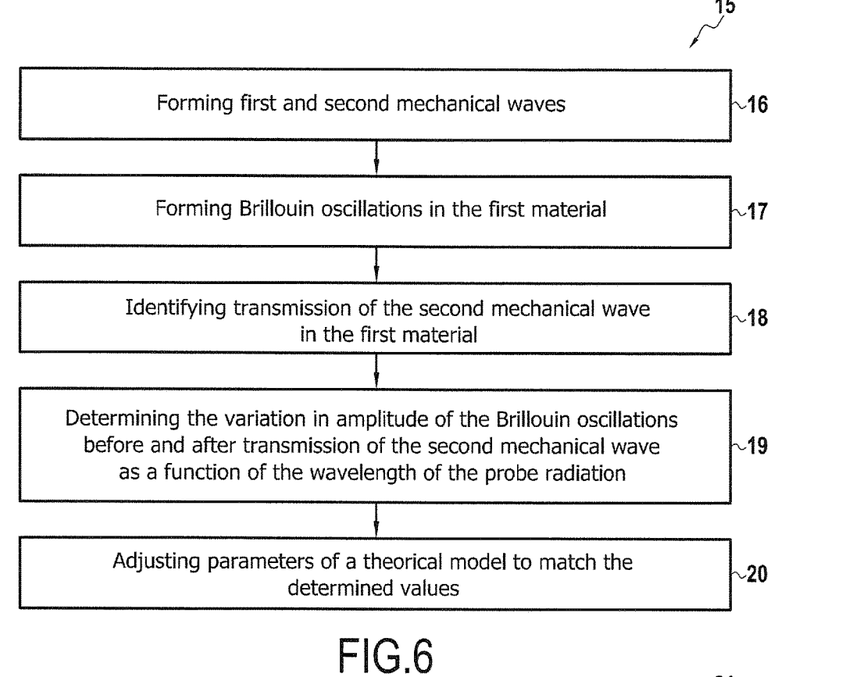
FIGS. 6 and 7 are examples of flow charts for implementations of methods of the invention.

FIG. 6 is a flow chart 15 of an implementation of a method of the invention for characterizing an interface between a first material and a second material.

In a first step 16, a first mechanical wave and a second mechanical wave are formed, and then in a second step 17, Brillouin oscillations are formed in the first material. Thereafter, in a third step 18, transmission of the second mechanical wave in the first material is identified, and during a fourth step 19, the variation in the amplitude of the Brillouin oscillations before and after transmission of the second mechanical wave is determined. The fourth step 19 may be performed in particular as a function of the wavelength of the probe radiation. Finally, in a preferred last step 20, the parameters of a theoretical model are adjusted to the values that have been determined.

Figure 7:
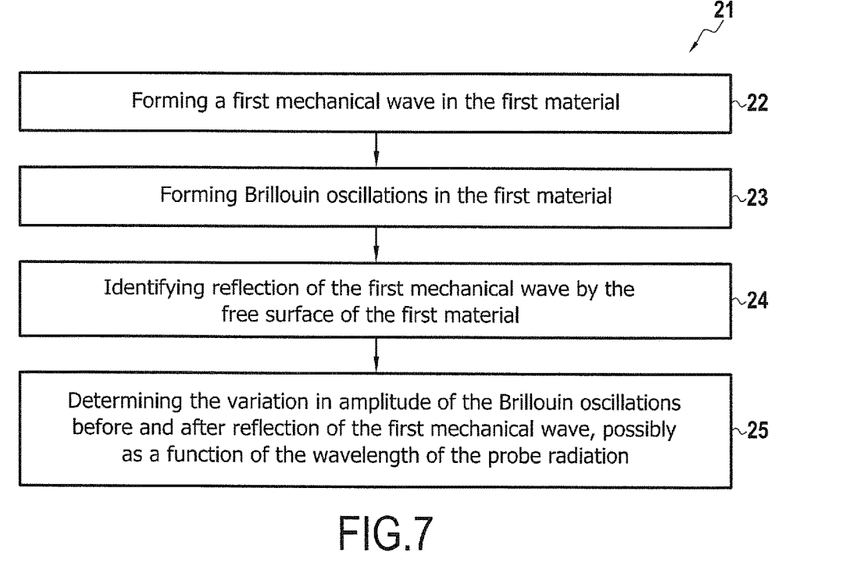

FIG. 7 shows a flow chart 21 of an implementation of a method of the invention for characterizing the roughness of a surface of a first material.

In a first step 22, a first mechanical wave is formed in the first material and then in a second step 23, Brillouin oscillations are formed in the first material. Then, in a third step 24, reflection of the first mechanical wave on the free surface of the first material is identified, and during a fourth step 25, the variation in the amplitude of the Brillouin oscillations before and after reflection of the first mechanical wave is determined. The fourth step 25 may in particular be performed as a function of the wavelength of the probe radiation.

Thus, the subject matter of the invention makes it possible in reliable and non-destructive manner to obtain characteristics of a structure, in particular the roughness of a surface reflecting a soundwave, or indeed the transmission coefficient at an interface between two materials. Furthermore, the use of a probe of variable wavelength makes it possible to refine the above characteristics, and to obtain easily values that are more accurate and more complete.

The invention claimed is:

1. A device configured to characterize an interface of a structure, said structure comprising a solid first material and a second material, which materials are separated by said interface, the device comprising:
   a generator configured to generate a first mechanical wave in the solid first material;
   a generator configured to generate probe radiation configured to propagate at least in part in the solid first material so as to form Brillouin oscillations; and
   a detector configured to detect the variation in time of the Brillouin oscillations in the solid first material;

wherein the device further comprises:
   an identification device configured to use the time variation of the Brillouin oscillations in the solid first material to identify reflection of said first mechanical wave by said interface or transmission through said interface of a second mechanical wave interfering with the first mechanical wave; and
   a determination device configured to determine the variation in amplitude of the Brillouin oscillations in the solid first material before and after reflection or transmission by said interface.

2. The device according to claim 1, wherein the determination device is configured to determine the variation in amplitude of the Brillouin oscillations as a function of the wavelength of the probe radiation.

3. The device according to claim 1, wherein the second material is a gas, and wherein:
   the identification device is configured to identify a reflection of said first mechanical wave by said interface; and
   the determination device is configured to determine the variation in amplitude of the Brillouin oscillations before and after reflection by said interface, in order to characterize the roughness of said interface.

4. The device according to claim 3, wherein the generator configured to generate probe radiation is configured to change the wavelength of the probe radiation as a function of the size of the roughness to be measured.

5. The device according to claim 1, wherein the second material is a solid thin layer, and wherein:
   the identification device is configured to identify transmission by said interface of a second mechanical wave interfering with the first mechanical wave; and
   the determination device is configured to determine the variation in amplitude of the Brillouin oscillations before and after transmission by said interface of the second mechanical wave, in order to characterize the acoustic transmission coefficient of said interface.

6. The device according to claim 5, wherein the generator configured to generate a first mechanical wave in the solid first material is configured to form the first and second mechanical waves simultaneously respectively in the solid first material and in the second material.

7. The device according to claim 5, further comprising an adjustment device configured to adjust parameters of a theoretical model giving the values for variation in amplitude of the Brillouin oscillations for different probe radiation wavelengths, in order to obtain the amplitude variation of the Brillouin oscillations as determined by the determination device, with the parameters as adjusted in this way serving to characterize the interface.

8. A method of characterizing an interface of a structure, said structure comprising a solid first material and a second material, which materials are separated by said interface, the method comprising the following steps:
   forming a first mechanical wave in the solid first material;
   generating a probe radiation;
   forming Brillouin oscillations with probe radiation propagating at least in part in the solid first material; and
   detecting the time variation of the Brillouin oscillations in the solid first material;
wherein the method further comprises the following steps:
   identifying reflection of said first mechanical wave by said interface or transmission through said interface of a second mechanical wave interfering with the first mechanical wave on the basis of the time variation of the Brillouin oscillations in the solid first material; and determining the variation in amplitude of the Brillouin oscillations in the solid first material before and after reflection or transmission by said interface.

9. The method according to claim 8, wherein the variation in amplitude of the Brillouin oscillations as a function of the wavelength of the probe radiation is determined.

10. The method according to claim 8, wherein the second material is a gas, and wherein a reflection of said first mechanical wave by said interface is identified, and the variation in amplitude of the Brillouin oscillations before and after reflection by said interface is determined in order to characterize the roughness of said interface.

11. The method according to claim 10, wherein the wavelength of the probe radiation is selected as a function of the size of the roughness to be measured.

12. The method according to claim 8, wherein the second material is a solid thin layer, and wherein transmission through said interface of a second mechanical wave interfering with the first mechanical wave is identified, and the variation in amplitude of the Brillouin oscillations before and after transmission by said interface of the second mechanical wave is determined in order to characterize the acoustic transmission coefficient of said interface.

13. The method according to claim 12, wherein the first and second mechanical waves are formed simultaneously respectively in the solid first material and in the second material.

14. The method according to claim 9, wherein the parameters of a theoretical model giving the values for variation in amplitude of the Brillouin oscillations for different wavelengths of the probe radiation are adjusted in order to obtain the variations in amplitude of the Brillouin oscillations as determined, with the parameters as adjusted in this way serving to characterize the interface.

* * * * *